United States Patent
Safai

(10) Patent No.: US 9,532,009 B1
(45) Date of Patent: Dec. 27, 2016

(54) SYSTEMS AND METHODS FOR DETECTING CONTAMINANTS USING LASER BEAM PATH LENGTH DIFFERENCES

(71) Applicant: The Boeing Company, Seal Beach, CA (US)

(72) Inventor: Morteza Safai, Newcastle, WA (US)

(73) Assignee: The Boeing Company, Chicago, IL (US)

( * ) Notice: Subject to any disclaimer, the term of this patent is extended or adjusted under 35 U.S.C. 154(b) by 422 days.

(21) Appl. No.: 13/860,288

(22) Filed: Apr. 10, 2013

(51) Int. Cl.
*H04N 7/18* (2006.01)

(52) U.S. Cl.
CPC ........................................ *H04N 7/18* (2013.01)

(58) Field of Classification Search
USPC .......................................................... 348/83
See application file for complete search history.

(56) References Cited

U.S. PATENT DOCUMENTS

| | | | |
|---|---|---|---|
| 3,994,603 A * | 11/1976 | Paschedag | 356/438 |
| 4,541,715 A * | 9/1985 | Akiyama et al. | 356/237.4 |
| 4,760,537 A * | 7/1988 | Martin et al. | 382/100 |
| 5,004,340 A * | 4/1991 | Tullis et al. | 356/243.6 |
| 5,078,901 A | 1/1992 | Sparrow | |
| 5,216,409 A * | 6/1993 | Ament et al. | 340/438 |
| 5,510,620 A * | 4/1996 | Achter et al. | 250/339.12 |
| 5,533,075 A * | 7/1996 | Jones et al. | 376/272 |
| 6,268,913 B1 * | 7/2001 | Rising | 356/326 |
| 6,542,242 B1 * | 4/2003 | Yost et al. | 356/450 |
| 6,664,796 B2 * | 12/2003 | Wang et al. | 324/694 |
| 6,693,275 B1 * | 2/2004 | Stork | G01B 11/06 250/223 B |
| 6,939,081 B1 | 9/2005 | Gropp | |
| 6,956,228 B2 * | 10/2005 | Shelley et al. | 250/559.4 |
| 7,473,352 B2 | 1/2009 | Sundeng | |
| 2004/0020271 A1 | 2/2004 | Hutchinson | |
| 2005/0122225 A1 * | 6/2005 | Kram et al. | 340/605 |
| 2006/0231501 A1 * | 10/2006 | Sundeng | 210/745 |
| 2009/0173698 A1 | 7/2009 | Sundeng | |

* cited by examiner

*Primary Examiner* — Leron Beck
(74) *Attorney, Agent, or Firm* — Armstrong Teasdale LLP

(57) ABSTRACT

A system for detecting a contaminant in a container is provided. The system includes a laser source configured to emit a laser beam into the container, an imaging array configured to detect the laser beam as imaging data, and a computing device communicatively coupled to the imaging array. The computing device is configured to determine, from the imaging data, a plurality of beam path length differences due to the contaminant, and calculate, from the beam path length differences, a volume of contaminant in the container.

17 Claims, 4 Drawing Sheets

SYSTEMS AND METHODS FOR DETECTING CONTAMINANTS USING LASER BEAM PATH LENGTH DIFFERENCES

BACKGROUND

The field of the disclosure relates generally to fuel storage, and more specifically, to detecting contaminants in a fuel container.

Fuel is stored and transported for use in a variety of applications. For example, fuel may be stored in a fuel tank on a vehicle, or pumped from a storage tank through a fuel line from a first location to a second location. However, contaminants present in the fuel container and/or entrained in the fuel may impact the quality and/or properties of the fuel, and/or may impact the operability of the fuel container itself. Such contaminants can include, for example, water, sand, and/or rust within the fuel container.

In at least some known fuel containment systems, it may not be possible to proactively determine whether contaminants are present. Rather, contaminants are typically identified only after the performance of one or more devices (e.g., engines) operating on the contaminated fuel is adversely impacted. For example, contaminated fuel may cause premature shut down of a vehicle engine. Accordingly, at least some known fuel containment systems are unable to detect the presence, much less the quantity, of contaminants in fuel stored therein. After contamination is detected, in at least some known fuel containment systems, the fuel container must be purged of all contaminated fuel and refilled with clean, uncontaminated fuel.

BRIEF DESCRIPTION

In one aspect, a system for detecting a contaminant in a container is provided. The system includes a laser source configured to emit a laser beam into the container, an imaging array configured to detect the laser beam as imaging data, and a computing device communicatively coupled to the imaging array. The computing device is configured to determine, from the imaging data, a plurality of beam path length differences due to the contaminant, and calculate, from the beam path length differences, a volume of contaminant in the container.

In another aspect, a computing device for use in detecting a contaminant in a container is provided. The computing device includes a memory device, and a processor communicatively coupled to the memory device, the processor configured to receive imaging data from an imaging array, the imaging data including a plurality of measured path lengths of a laser beam transmitted through the container, determine, from the imaging data, a plurality of beam path length differences due to the contaminant, and calculate, from the beam path length differences, a volume of contaminant in the container.

In yet another aspect, a method for detecting a contaminant in a container is provided. The method includes emitting a laser beam into the container such that the laser beam passes through at least a portion of the container, detecting the laser beam as imaging data using an imaging array, the imaging data including a plurality of measured path lengths of the laser beam, determining, from the imaging data, a plurality of beam path length differences due to the contaminant, and calculating, from the path length differences, a volume of contaminant in the container.

The features, functions, and advantages that have been discussed can be achieved independently in various implementations or may be combined in yet other implementations, further details of which can be seen with reference to the following description and drawings.

DETAILED DESCRIPTION

The systems and methods described herein enable detecting a contaminant in a liquid, such as fuel, stored in a container, such as a fuel tank or a fuel line. A laser beam is emitted into the fuel container. After passing through potentially contaminated liquid, the laser beam is detected by an imaging array. Based on path length differences of the laser beam that are due to the contaminant, the volume of contaminant in the fuel container is calculated.

Technical effects of the methods and systems described herein include at least one of: (a) receiving imaging data from an imaging array, the imaging data including a plurality of measured path lengths of a laser beam transmitted through at least a portion of the container; (b) determining, from the imaging data, a plurality of beam path length differences due to the contaminant; and (c) calculating, from the path length differences, a volume of contaminant in the container.

Figure 1:
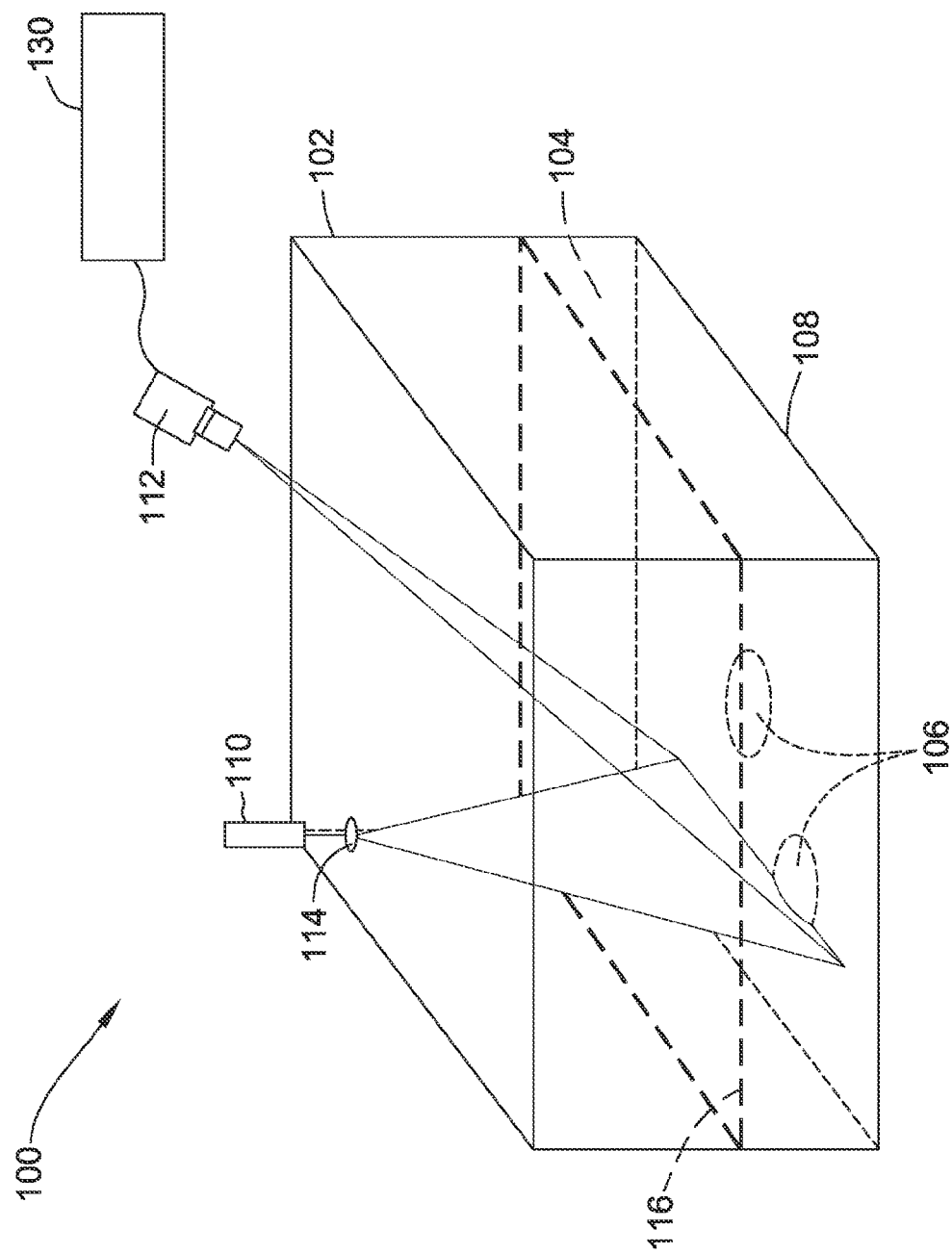
FIG. 1 is a schematic diagram of an exemplary contaminant detection system.

FIG. 1 is a schematic diagram of an exemplary contaminant detection system 100 for detecting a contaminant in a fuel container 102. In the exemplary implementation, fuel container 102 is at least partially filled with fuel 104. Fuel container 102 may include any vessel capable of holding fuel 104 (e.g., a fuel tank for storing fuel 104 for a period of time, a fuel line for transporting fuel 104 from one location to another, etc.). In some implementations, fuel container 102 may be located onboard a vehicle, such as an automobile, boat, or aircraft.

One or more contaminants 106 may be located in fuel container 102. For example, unfrozen water may accumulate on a bottom 108 of fuel container 102. Contaminants 106 may dilute and/or otherwise undesirably interact with fuel 104. Accordingly, it may be beneficial to accurately detect an amount of contaminants 106 in fuel container 102. In the exemplary implementation, contaminant 106 is water in a liquid state or solid state (i.e., ice) Alternatively, contaminant 106 may be any substance capable of detection using the systems and methods described herein. For example, contaminant 106 may include sealant, rust, and/or sand that has settled within fuel container 102. In FIG. 1, contaminant 106 is two water droplets.

Although in the exemplary implementation, contaminant 106 is located in fuel 104 in fuel container 102, the methods and systems described herein may be utilized to locate contaminant 106 in any liquid within a container wherein the liquid has a different index of refraction than contaminant 106. Further, although contaminant 106 is on bottom 108 of fuel container 102 in the exemplary implementation, contaminant 106 may be located at other locations within fuel 104 (e.g., suspended and/or floating within fuel 104).

In the exemplary implementation, contaminants 106 are detected using a laser scan head 110 and an imaging array 112. Laser scan head 110 emits a laser beam at a pre-selected wavelength. Laser scan head 110 may be mounted to a support member (not shown) or hand-held.

The laser beam passes through line scanning optics 114 that convert the laser beam from a point to a line format. The converted laser beam passes through a surface 116 of fuel 104 in fuel container 102. In the exemplary implementation, where contaminant 106 is water, laser scan head 110 emits a laser beam having a wavelength that is substantially optically transparent to fuel 104 but substantially optically opaque to water 106. For example, the laser beam may have a wavelength in a range of 480 nanometers (nm) to 620 nm. Accordingly, the emitted laser beam passes through fuel 104 without significant perturbation, but bends when entering water 106 due to a change in the index of refraction. The laser beam reflects off of bottom 108, and bends again when exiting water 106 due to the change in the index of refraction.

To identify all contaminants 106 on bottom 108, laser scan head 110 may rotate such that the line format laser beam scans along entire bottom 108. In implementations where fuel container 102 is a fuel line with a mixture of fuel 104 and contaminants 106 flowing therethrough, laser scan head 110 may remain fixed (i.e., non-rotating) as the mixture flows past.

Imaging array 112 detects the reflected laser beam, and may include any suitable imaging sensor, including, but not limited to, a charge-coupled device (CCD) sensor, a complementary metal-oxide-semiconductor (CMOS) sensor, and/or a charge injection device (CID) sensor. Further, imaging array 112 may include a color imaging sensor or a black and white imaging sensor. In the exemplary implementation, imaging array 112 is a two-dimensional imaging array (e.g., 500 pixels by 500 pixels) that can detect the reflected laser beam from anywhere on bottom 108. Alternatively, imaging array 112 may be a one-dimensional array (e.g., 500 pixels by 1 pixel) that rotates in conjunction with laser scan head 110 to map any contaminants 106 on bottom 108. Imaging array 112 is communicatively coupled to a computing device 130 that processes imaging data (i.e., the reflected laser beam) detected by imaging array 112.

Figure 2:
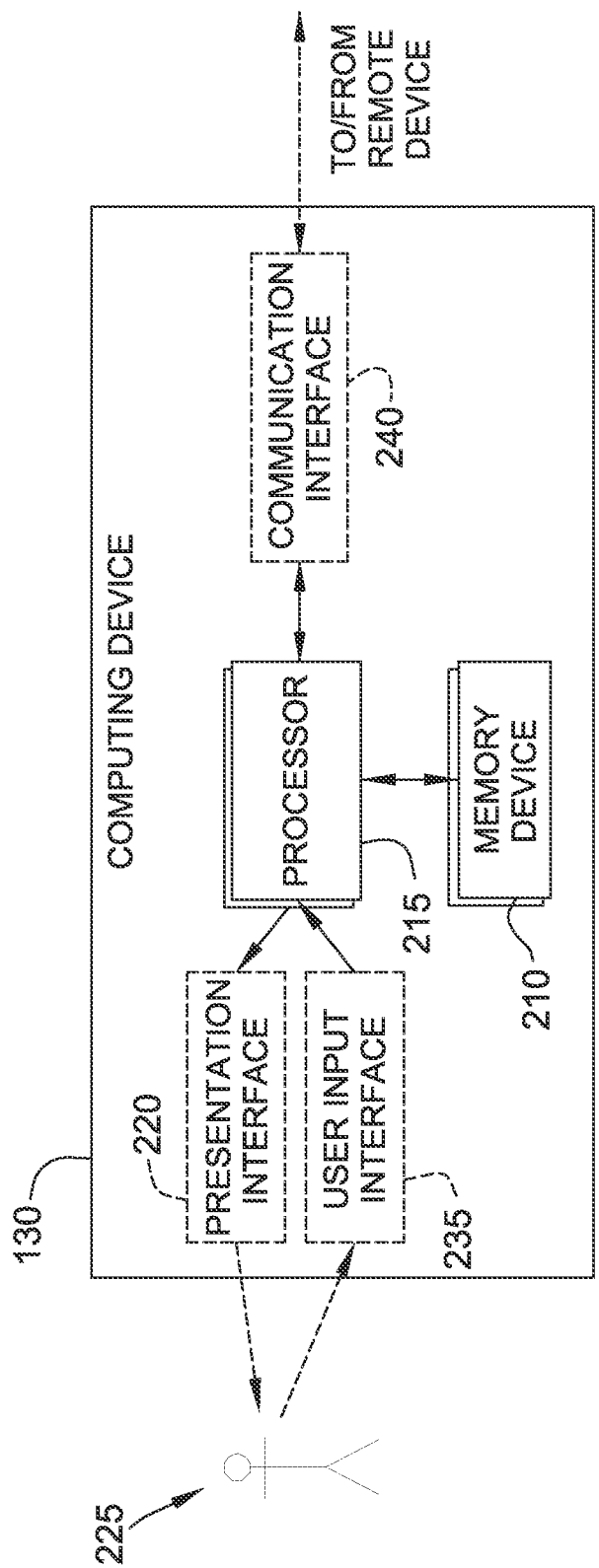
FIG. 2 is a block diagram of an exemplary computing device that may be used with the system shown in FIG. 1.

FIG. 2 is a block diagram of computing device 130 that may be used with contaminant detection system 100 (shown in FIG. 1). Computing device 130 includes at least one memory device 210 and a processor 215 that is coupled to memory device 210 for executing instructions. In some implementations, executable instructions are stored in memory device 210. In the exemplary implementation, computing device 130 performs one or more operations described herein by programming processor 215. For example, processor 215 may be programmed by encoding an operation as one or more executable instructions and by providing the executable instructions in memory device 210.

Processor 215 may include one or more processing units (e.g., in a multi-core configuration). Further, processor 215 may be implemented using one or more heterogeneous processor systems in which a main processor is present with secondary processors on a single chip. In another illustrative example, processor 215 may be a symmetric multi-processor system containing multiple processors of the same type. Further, processor 215 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein. In the exemplary implementation, processor 215 processes imaging data from imaging array 112 to determine a quantity of contaminants 106 in fuel container 102, as described herein.

In the exemplary implementation, memory device 210 is one or more devices that enable information such as executable instructions and/or other data to be stored and retrieved. Memory device 210 may include one or more computer readable media, such as, without limitation, dynamic random access memory (DRAM), static random access memory (SRAM), a solid state disk, and/or a hard disk. Memory device 210 may be configured to store, without limitation, application source code, application object code, source code portions of interest, object code portions of interest, configuration data, execution events and/or any other type of data.

In the exemplary implementation, computing device 130 includes a presentation interface 220 that is coupled to processor 215. Presentation interface 220 presents information to a user 225. For example, presentation interface 220 may include a display adapter (not shown) that may be coupled to a display device, such as a cathode ray tube (CRT), a liquid crystal display (LCD), an organic LED (OLED) display, and/or an "electronic ink" display. In some implementations, presentation interface 220 includes one or more display devices.

In the exemplary implementation, computing device 130 includes a user input interface 235. User input interface 235 is coupled to processor 215 and receives input from user 225. User input interface 235 may include, for example, a keyboard, a pointing device, a mouse, a stylus, a touch sensitive panel (e.g., a touch pad or a touch screen), a gyroscope, an accelerometer, a position detector, and/or an audio user input interface. A single component, such as a touch screen, may function as both a display device of presentation interface 220 and user input interface 235.

Computing device 130, in the exemplary implementation, includes a communication interface 240 coupled to processor 215. Communication interface 240 communicates with one or more remote devices. To communicate with remote devices, communication interface 240 may include, for example, a wired network adapter, a wireless network adapter, and/or a mobile telecommunications adapter.

In the exemplary implementation, processor 215 determines a path length difference of the reflected laser beam due to contaminant 106. The path length difference may be determined by calculating the difference between a path length detected by imaging array 112 and a predetermined calibration path length. For example, the calibration path length may be obtained by mapping bottom 108 when no contaminant 106 is present. The calibration path length may be stored, for example, in memory device 210.

From the path length difference, processor 215 can determine the position of contaminant 106 on bottom 108. More specifically, in the exemplary implementation, processor 215 determines a profile of contaminant 106 on bottom 108 from the path length difference. From the profile, processor 215 can determine the quantity (e.g., volume) of contaminant 106 in fuel container 102, as described herein.

Figure 3:
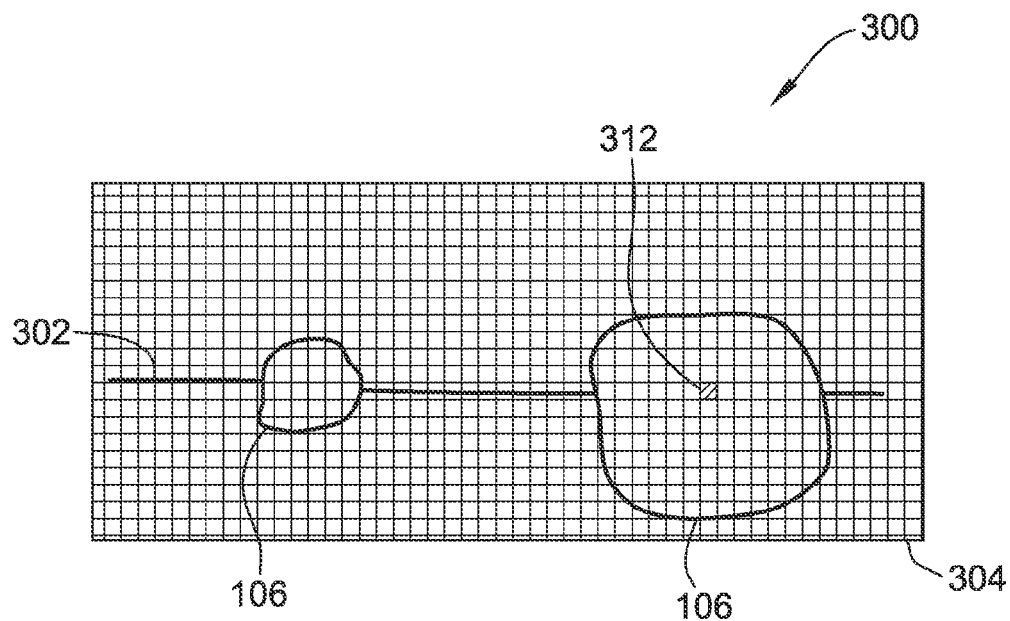
FIG. 3 is an exemplary horizontal profile obtained using the system shown in FIG. 1.
Figure 4:
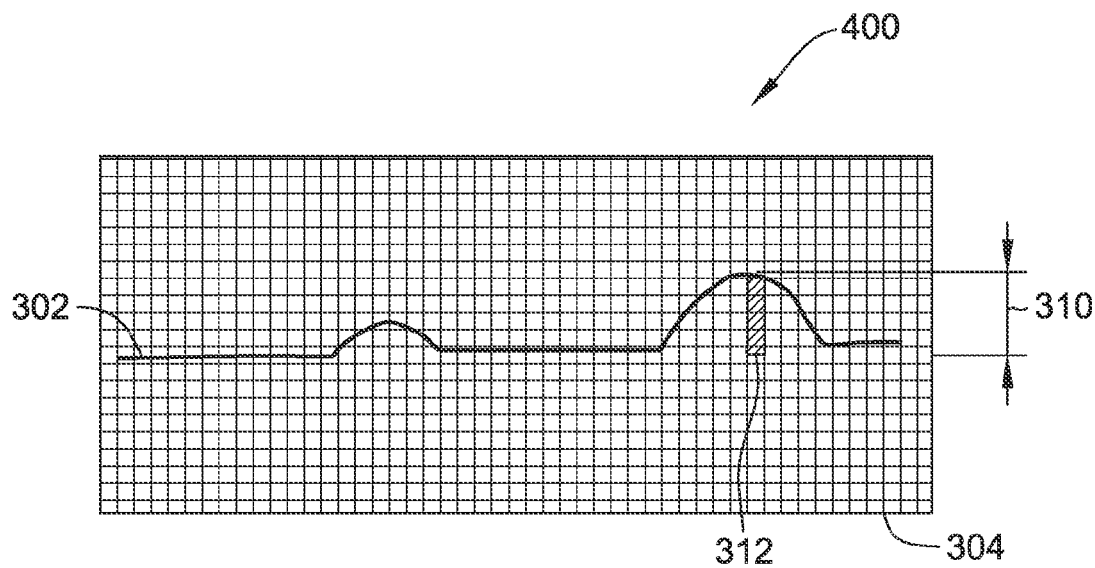
FIG. 4 is an exemplary vertical profile obtained using the system shown in FIG. 1.

FIG. 3 is a horizontal profile 300 of the two water droplets of contaminant 106. FIG. 4 is a vertical profile 400 of the two water droplets of contaminant 106 taken along a slice line 302 in horizontal profile 300. Horizontal and vertical profiles 300 and 400 are subdivided into a plurality of pixels 304. In at least some implementations, horizontal profile 300 and/or vertical profile 400 is displayed on presentation interface 220.

From horizontal profile 300 and vertical profile 400, processor 215 calculates the volume of the two water droplets. In the exemplary implementation, processor 215 calculates the volume by multiplying each pixel 304 in horizontal profile 300 that includes contaminant by a corresponding height 310 in vertical profile 400. For example, suppose each pixel 304 in vertical profile 400 has a height of 1 centimeter (cm), and each pixel 304 in horizontal profile 300 corresponds to an area of 1 cm². For a particular pixel 312 of in horizontal profile 300, the corresponding height 310 in vertical profile 400 is approximately four pixels. Accordingly, the volume of contaminant 106 for particular pixel 312 is equal to 1 cm²×4 cm, or 4 milliliters (ml). Performing the same calculation for each pixel 304 in horizontal profile 300 that includes contaminant 106 and summing the results gives the total volume of contaminant 106 in fuel container 102. Alternatively, processor 215 may calculate the volume of contaminant 106 using any method that enables system 100 to function as described herein. For example, in one implementation, processor 215 approximates each droplet as a cylinder, and calculates the volume as an area of a base of the droplet multiplied by a peak height of the droplet.

In the exemplary implementation, processor 215 compares the calculated contaminant volume to a predetermined threshold volume stored, for example, on memory device 210. If the calculated contaminant volume is above the predetermined threshold volume, processor 215 may generate an alarm to alert user 225. The alarm may include any audio and/or visual indication that facilitates alerting user 225. In response to the generated alarm, user 225 may take appropriate actions to attempt to reduce the amount of contaminant 106 in fuel container 102.

Figure 5:
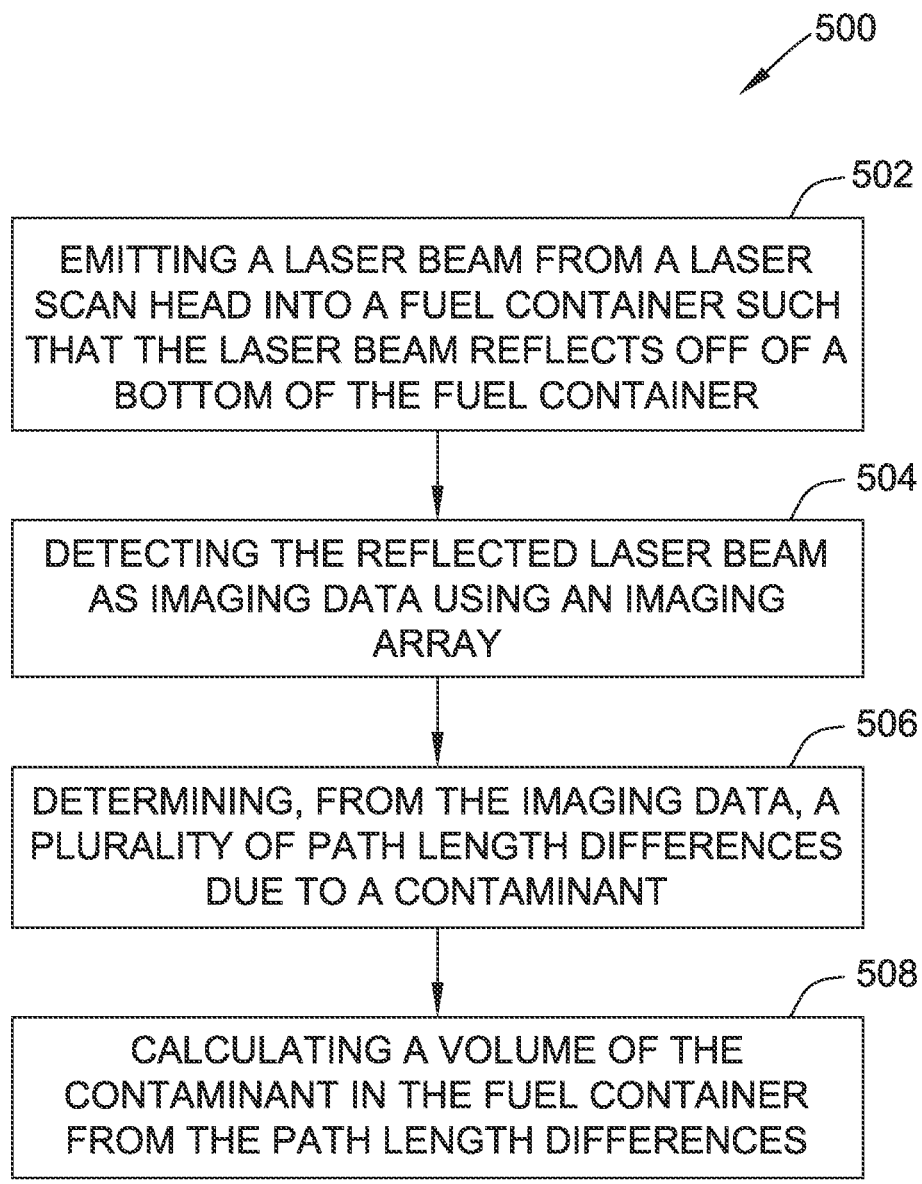
FIG. 5 is a flow chart of an exemplary method for detecting an amount of a contaminant that may be used with the system shown in FIG. 1.

FIG. 5 is a flowchart of an exemplary method 500 for detecting an amount of contaminant in a fuel container, such as fuel container 102 (shown in FIG. 1). Method 500 includes emitting 502 a laser beam into the fuel container such that the laser beam reflects off a bottom of the fuel container. The laser beam may be emitted 502 using a laser scan head, such as laser scan head 110 (shown in FIG. 1). The reflected laser beam is detected 504 as imaging data using an imaging array, such as imaging array 112 (shown in FIG. 1). In the exemplary implementation, the imaging data is a plurality of measured path lengths of the laser beam.

A plurality of path length differences due to the contaminant are determined 506 from the imaging data. The path length differences may be determined 506 using, for example, a processor, such as processor 215 (shown in FIG. 2). From the path length differences, a volume of the contaminant in the fuel container is calculated 508. In the exemplary implementation, the processor calculates 508 the volume of the contaminant in the fuel container.

The implementations described herein enable detecting a contaminant in a liquid, such as fuel, stored in a container, such as a fuel tank or a fuel line. A laser beam is emitted into the fuel container. After passing through potentially contaminated liquid, the laser beam is detected by an imaging array. Based on path length differences of the laser beam that are due to the contaminant, the volume of contaminant in the fuel container is calculated.

Unlike at least some known fuel containment systems, the systems and methods described herein enable detecting contamination before the contamination affects operability of the fuel container and/or one or more devices that operate using the fuel. Further, as compared to at least some known fuel containment systems, using the systems and methods described herein, in addition to detecting the presence of a contaminant, the quantity (e.g., volume) of the contaminant can also be detected.

The implementations described herein may utilize executable instructions embodied in a computer readable medium, including, without limitation, a storage device or a memory area of a computing device. Such instructions, when executed by one or more processors, cause the processor(s) to perform at least a portion of the methods described herein. As used herein, a "storage device" is a tangible article, such as a hard drive, a solid state memory device, and/or an optical disk that is operable to store data.

Although specific features of various implementations of the invention may be shown in some drawings and not in others, this is for convenience only. In accordance with the principles of the invention, any feature of a drawing may be referenced and/or claimed in combination with any feature of any other drawing.

This written description uses examples to disclose various implementations, which include the best mode, to enable any person skilled in the art to practice those implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for detecting a contaminant in a container, said system comprising:
   a laser source configured to emit a laser beam into the container;
   an imaging array configured to detect the laser beam reflected from a surface of the container, said imaging array configured to determine imaging data from the laser beam; and
   a computing device communicatively coupled to said imaging array, said computing device configured to:
      store, in a memory device, a plurality of predetermined calibration path lengths that were previously obtained when no contaminant was present in the container;
      determine, from the imaging data, a plurality of measured reflected beam path lengths when the contaminant is present in the container;
      calculate a plurality of beam path length differences due to the contaminant, wherein each beam path length difference is calculated as a difference between a measured reflected beam path length of the plurality of measured reflected beam path lengths and a corresponding predetermined calibration path length of the plurality of predetermined calibration path lengths, wherein said computing device is configured to calculate the plurality of beam path length differences due to the contaminant, wherein the laser beam bends when passing through the contaminant such that the measured reflected beam length is greater than the corresponding predetermined calibration path length; and
      calculate, from the beam path length differences, a volume of contaminant in the container.

2. A system in accordance with claim 1, further comprising line scanning optics configured to convert the emitted laser beam into a line format.

3. A system in accordance with claim 1, wherein said laser source is configured to scan a bottom of the container with the laser beam.

4. A system in accordance with claim 1, wherein said laser source is configured to emit a laser beam having a wavelength that is substantially optically transparent to fuel and that is substantially optically opaque to the contaminant.

5. A system in accordance with claim 4, wherein the contaminant is water in at least one of a liquid state and a solid state.

6. A system in accordance with claim 1, wherein said imaging array is one of a one-dimensional imaging array and a two-dimensional imaging array.

7. A system in accordance with claim 1, wherein the container is part of an aircraft.

8. A computing device for use in detecting a contaminant in a container, said computing device comprising:
   a memory device; and
   a processor communicatively coupled to said memory device, said processor configured to:
      receive imaging data from an imaging array, the imaging data including a plurality of measured reflected beam path lengths of a laser beam transmitted into the container and reflected from a surface of the container when the contaminant is present in the container;
      store, in said memory device, a plurality of predetermined calibration path lengths that were previously obtained when no contaminant was present in the container;
      calculate a plurality of beam path length differences due to the contaminant, wherein each beam path length difference is calculated as a difference between a measured reflected beam path length of the plurality of measured reflected beam path lengths and a corresponding predetermined calibration path length of the plurality of predetermined calibration path lengths, wherein said computing device is configured to calculate the plurality of beam path length differences due to the contaminant, wherein the laser beam bends when passing through the contaminant such that the measured reflected beam length is greater than the corresponding predetermined calibration path length; and
      calculate, from the beam path length differences, a volume of contaminant in the container.

9. A computing device in accordance with claim 8, wherein to calculate a volume of the contaminant, said processor is configured to:
   generate at least one profile of a bottom of the container from the plurality of beam path length differences; and
   calculate the volume of contaminant from the at least one generated profile.

10. A computing device in accordance with claim 9, further comprising a presentation interface communicatively coupled to said processor, said presentation interface configured to display the at least one generated profile.

11. A computing device in accordance with claim 9, wherein to generate at least one profile of a bottom of the container, said processor is configured to generate a horizontal profile and a plurality of vertical profiles.

12. A computing device in accordance with claim 9, wherein said processor is further configured to:
   compare the calculated volume of contaminant to a predetermined threshold volume stored on said memory device; and
   generate an alarm when the calculated volume of contaminant exceeds the predetermined threshold volume.

13. A method for detecting a contaminant in a container, said method comprising:
   emitting a laser beam into the container such that the laser beam passes through at least a portion of the container;
   detecting the laser beam reflected from a surface of the container as imaging data using an imaging array, the imaging data including a plurality of measured reflected path lengths of the laser beam when the contaminant is present in the container;
   storing, in a memory device, a plurality of predetermined calibration path lengths that were previously obtained when no contaminant was present in the container;
   calculate a plurality of beam path length differences due to the contaminant, wherein each beam path length difference is calculated as a difference between a measured reflected beam path length of the plurality of measured reflected beam path lengths and a corresponding predetermined calibration path length of the plurality of predetermined calibration path lengths, wherein said computing device is configured to calculate the plurality of beam path length differences due to the contaminant, wherein the laser beam bends when passing through the contaminant such that the measured reflected beam length is greater than the corresponding predetermined calibration path length; and
   calculating, from the path length differences, a volume of contaminant in the container.

14. A method in accordance with claim 13, wherein emitting a laser beam comprises emitting a laser beam having a wavelength that is substantially optically transparent to fuel and substantially optically opaque to the contaminant.

15. A method in accordance with claim 13, further comprising rotating a laser source that emits the laser beam to scan a bottom of the container with the laser beam.

16. A method in accordance with claim 13, wherein detecting the laser beam comprises detecting the laser beam using a two-dimensional imaging array after the laser beam has reflected off of a bottom of the container.

17. A method in accordance with claim 13, further comprising:
   comparing the calculated volume of contaminant to a predetermined threshold volume; and
   generating an alarm when the calculated volume of contaminant exceeds the predetermined threshold volume.

\* \* \* \* \*

UNITED STATES PATENT AND TRADEMARK OFFICE
CERTIFICATE OF CORRECTION

PATENT NO. : 9,532,009 B1
APPLICATION NO. : 13/860288
DATED : December 27, 2016
INVENTOR(S) : Morteza Safai It is certified that error appears in the above-identified patent and that said Letters Patent is hereby corrected as shown below:

In the Claims

In Column 8, Line 25, Claim 13, delete "calculate a plurality" and insert therefor -- calculating a plurality --.

Signed and Sealed this
Eighteenth Day of July, 2017

Joseph Matal
*Performing the Functions and Duties of the
Under Secretary of Commerce for Intellectual Property and
Director of the United States Patent and Trademark Office*